US012642796B2

(12) United States Patent
Vasisht

(10) Patent No.: US 12,642,796 B2
(45) Date of Patent: Jun. 2, 2026

(54) METHOD AND DEVICE OF TREATING CHRONIC KIDNEY DISEASE-ASSOCIATED PRURITUS

(71) Applicant: Avior, Inc., Cary, NC (US)

(72) Inventor: Niraj Vasisht, Cary, NC (US)

(73) Assignee: Avior, Inc., Cary, NC (US)

( * ) Notice: Subject to any disclaimer, the term of this patent is extended or adjusted under 35 U.S.C. 154(b) by 574 days.

(21) Appl. No.: 17/285,971

(22) PCT Filed: Oct. 17, 2019

(86) PCT No.: PCT/US2019/056635

§ 371 (c)(1),
(2) Date: Apr. 16, 2021

(87) PCT Pub. No.: WO2020/081754

PCT Pub. Date: Apr. 23, 2020

(65) Prior Publication Data

US 2021/0369703 A1 Dec. 2, 2021

Related U.S. Application Data

(60) Provisional application No. 62/747,506, filed on Oct. 18, 2018.

(51) Int. Cl.
*A61P 17/04* (2006.01)
*A61K 9/00* (2006.01)
*A61K 9/70* (2006.01)
*A61K 31/485* (2006.01)

(52) U.S. Cl.
CPC ............ *A61K 31/485* (2013.01); *A61K 9/006* (2013.01); *A61K 9/7007* (2013.01); *A61P 17/04* (2018.01)

(58) Field of Classification Search
None
See application file for complete search history.

(56) References Cited

U.S. PATENT DOCUMENTS 4,946,848 A 8/1990 Tuttle et al.
5,800,832 A 9/1998 Tapolsky et al.
5,948,430 A 9/1999 Zerbe et al.
6,103,266 A 8/2000 Tapolsky et al.
6,881,745 B2 4/2005 Hayes et al.
7,923,454 B2 4/2011 Wu et al.
8,987,289 B2 * 3/2015 Sciascia ............... A61K 31/485 514/282
9,265,160 B2 2/2016 Paul et al.
9,339,499 B2 5/2016 Hartman et al.
9,522,188 B2 12/2016 Finn et al.
9,901,545 B1 2/2018 Fuisz et al.
10,195,142 B2 2/2019 Fuisz et al.
10,238,600 B2 3/2019 Fuisz et al.
11,318,107 B2 5/2022 Vasisht et al.
11,504,342 B2 11/2022 Vasisht et al.
2006/0134144 A1 6/2006 Chung et al.
2007/0148097 A1 6/2007 Finn
2008/0260807 A1 10/2008 Sharp et al.
2011/0129533 A1 6/2011 Straub et al.
2011/0262522 A1 10/2011 Finn et al.
2012/0009260 A1 1/2012 Schobel et al.
2012/0114705 A1 5/2012 Zerbe et al.
2012/0164191 A1 6/2012 Finn et al.
2013/0045268 A1 2/2013 Finn et al.
2014/0008831 A1 1/2014 Vang et al.
2014/0271787 A1 9/2014 Bogue
2014/0271867 A1 9/2014 Myers
2016/0128947 A1 5/2016 Mcconville et al.
2016/0235769 A1 8/2016 Hill
2017/0136078 A1 5/2017 Li et al.
2019/0105291 A1 4/2019 Boudes et al.

FOREIGN PATENT DOCUMENTS

CA 2274893 A1 6/1998
DE 19646392 A1 5/1998
EP 1462095 A1 9/2004
JP 2004043450 A 2/2004
MX 2020008694 A 1/2021
WO 03015783 A1 2/2003
WO 2003015783 A1 2/2003
(Continued)

OTHER PUBLICATIONS

Bergasa et al. (Oral nalmefene therapy reduces scratching activity due to the pruritus of cholestasis: A controlled study, Journal of American Academy of Dermatolgoy, vol. 41, Issue 3, Sep. 1999, pp. 431-434) (Year: 1999).*
Bergasa et al. (Oral nalmefene therapy reduces scratching activity due to the pruritus of cholestasis: A controlled study, Journal of American Academy of Dermatology, vol. 41, Issue 3, Sep. 1999, pp. 431-434) (Year: 1999).*
WIPO; International Preliminary Report on Patentability for International Patent Application No. PCT/US2019/056635 dated Apr. 29, 2021, 13 pages.
"Annual Report 2013: Perspectives", ESRD Patients, Fresenius Medical Care, 2014.
(Continued)

*Primary Examiner* — Melissa S Mercier

(74) *Attorney, Agent, or Firm* — COOLEY LLP; Sean Coughlin; Jennifer Mandal

(57) ABSTRACT

The presently disclosed subject matter is directed to an effective method of treating chronic kidney disease-associated pruritus. Particularly, the method comprises the transmucosal administering of nalmefene to treat chronic kidney disease-associated pruritus, as well as cholestatic pruritus and/or prurigo nodularis. The nalmefene can be configured in a single layer film comprising at least two distinct domains. The film can include a first discrete domain comprising about 50-100 weight percent polymer matrix and the second discrete domain can comprise the nalmefene or pharmaceutically acceptable nalmefene salt.

13 Claims, 9 Drawing Sheets

(56) References Cited

FOREIGN PATENT DOCUMENTS

| | | | | | |
|---|---|---|---|---|---|
| WO | WO2003015783 | | * | 2/2003 | |
| WO | WO-2014151915 | A1 | * | 9/2014 | ............. A61K 47/10 |
| WO | 2014209962 | A1 | | 12/2014 | |
| WO | 2017132752 | A1 | | 8/2017 | |
| WO | 2018005695 | A1 | | 1/2018 | |
| WO | 2019165208 | A1 | | 8/2019 | |

OTHER PUBLICATIONS

EPO; Extended European Search Report for European Patent Application No. EP 19873052.5 dated Jun. 30, 2022, 14 pages.

Bergasa, Nora V., et al., "Oral nalmefene therapy reduces scratching activity due to the pruritus of cholestasis: A controlled study", Journal of the American Academy of Dermatology, Mosby, Inc, vol. 41, No. 3, Sep. 14, 1999, 4 pages.

CNIPA, First Office Action for corresponding Chinese Patent Application No. 201980078491.2, mailed Apr. 26, 2023, 19 pages.

IPI; Examination Report for Indian Patent Application No. 202117020692 dated Nov. 1, 2022, 5 pages.

ISA/US; International Search Report and Written Opinion for International Patent Application No. PCT/US19/56635 dated Feb. 17, 2020, 16 pages.

Johnson, Curtis A., "2010 Dialysis of Drugs", Jan. 1, 2010, 3 pages.

"Nalbuphine", Wikipedia, Sep. 23, 2018, 7 pages, accessed at: https://enwikpedia.org/w/index.php?title=Nalbuphine&oldid=86093841.

Pisoni, Ronald L., et al., "Pruritus in Hemodialysis patients: International Results from the Dialysis Outcomes and Practical Pattern Study," Nephrol Dial Transplant, Sep. 2006, 11 pages.

Coresh, Josef, et al., "Prevalence of Chronic Kidney Disease in the United States", JAMA, Nov. 7, 2007, vol. 298, No. 17, 10 pages.

Baxter, "Revex (nalmefene hydrochoride injection)", Prescribing Information, 11 pages, accessed at: https://www.accessdata.fda.gov/drugsatfda_docs/label/2006/020459s006lbl.pdf.

"Cara Therapeutics Doses First Patient in Second Pivotal Phase 3 Efficacy Trial of KORSUVA™ (CR845/difelikefalin) Injection in Hemodialysis Patients with Chronic Kidney Disease-Associated Pruritus", Cara Therapeutics, Press Release, Aug. 7, 2018, 4 pages, accessed at: http://ir.caratherapeutics.com/news-releases/news-release-details/cara-therapeutics-doses-first-patient-second-pivotal-phase-3.

"Trevi Therapeutics Raises $50 Million Series C Financing Led by New Enterprise Associates", trevi Therapeutics, Jul. 20, 2017, Press Release, 2 pages, accessed at: https://www.trevitherapeutics.com/wp-content/uploads/2019/01/TreviSeriesC_PressRelease_072017.FINAL_. pdf.

Lee, H., et al., "Effects of Butorphanol on Morphine-induced Itch and Analgesia in Primates", Anesthesiology, Sep. 2007; vol. 107, No. 3, 16 pages.

Charuluxananan, S., et al., "Nalbuphine versus Propofol for Treatment of Intrathecal Morphine-Induced Pruritus After Cesarean Delivery," Anesthesiology & Analgesia, Jul. 2001; vol. 93, 4 pages.

Charuluxananan, S., et al., "Nalbuphine Versus Ondansetron for Prevention of Intrathecal Morphine-Induced Pruritus After Cesarean Delivery," Anesthesiology & Analgesia, Jun. 2003, vol. 96, 5 pages.

JPO; Office Action from Corresponding JP Patent Application No. 2021-521286, mailed Oct. 3, 2023, 3 pages.

MPO; Office Action from Corresponding MX Patent Application No. MX/a/2021/004405, mailed Mar. 11, 2024, 7 pages.

"Alpha-Tocopheryl acetate"—Surfactant, SAAPedia [online] retrieved on Feb. 16, 2021 from: http://www.saapedia.org/en/saa/?type=detail&id=5910, 2021, 5 pages.

Hennequin et al., "A new approach to studying inhibitors of calcium oxalate crystal growth", Urological Research, 1993, 21(2):101-108.

International Search Report and Written Opinion received for PCT Application No. PCT/US2019/019150, mailed on May 31, 2019, 21 pages.

International Search Report and Written Opinion received for PCT Application No. PCT/US2025/031191, mailed on Aug. 6, 2025, 12 pages.

International Preliminary Report on Patentability received for PCT Application No. PCT/US2019/019150, mailed on Sep. 3, 2020, 18 pages.

JP Application No. 2024-167408, Office Action mailed Jul. 17, 2025, with English translation, Applicant Avior, Inc.; 17 total pages.

Takahiro, Sato, "Pathophysiology and Management of Pruritus," The Japanese Journal of Dermatology, Feb. 2012, vol. 122, No. 2 (Feb. 2012), with English translation, 15 total pages.

* cited by examiner

METHOD AND DEVICE OF TREATING CHRONIC KIDNEY DISEASE-ASSOCIATED PRURITUS

CROSS-REFERENCE TO RELATED APPLICATIONS

This application is a U.S. National Stage of International Patent Application No. PCT/US19/56635, filed Oct. 17, 2019, which claims the benefit of U.S. Provisional Patent Application No. 62/747,506, filed Oct. 18, 2018, the entire contents of which are hereby incorporated herein by reference.

TECHNICAL FIELD

The presently disclosed subject matter relates to a method and device of treating chronic kidney disease-associated pruritus. Particularly, the presently disclosed subject matter includes transmucosal film compositions comprising nalmefene that can be administered buccally or sublingually to a subject in need of treatment.

BACKGROUND

Pruritus occurs in many diseases and conditions, such as chronic kidney disease. Particularly, chronic kidney disease-associated pruritus is common in patients suffering from chronic kidney dysfunction, occurring in about 20%-50% of patients. To this end, over 4.1 million patients in the United States suffer from pruritus associated with chronic kidney disease[1,2]. The presence of pruritus has been associated with poor quality of life, inadequate sleep, depression, and up to 37% higher adjusted mortality risk than patients with mild or no pruritus[3]. In addition, patients often develop prurigo nodularis[4,6], a skin disease characterized by inflamed, scaly, and excoriated nodules and lesions[6]. While the mild form of pruritus and prurigo nodularis is commonly treated with corticosteroids and antihistamines, such drugs are relatively ineffective in moderate and/or severe forms of chronic pruritus in both cholestatic (liver) and uremic (kidney) patients[7]. As a result, clinicians commonly use a variety of off-label medications for treatment[8]. Approximately 18% of the patients suffering from chronic kidney disease experience severe pruritus that cannot be a managed by current treatment methods. Further, there are no approved products in the United States to treat chronic kidney disease-associated pruritus, cholestatic pruritus, or prurigo nodularis. It would therefore be beneficial to provide an improved method of treating uremic pruritus and associated conditions, such as through the use of a transmucosal film device.

SUMMARY

In some embodiments, the presently disclosed subject matter is directed to a method of treating pruritus in a subject. Particularly, the method comprises transmucosally administering to a subject in need of such treatment a therapeutically effective amount of nalmefene or a pharmaceutically acceptable salt thereof.

In some embodiments, the subject has pruritus as a symptom of chronic kidney disease, reduced renal function, liver disease, prurigo nodularis, or combinations thereof.

In some embodiments, the treatment of pruritus decreases the level of Substance P in the subject.

In some embodiments, the subject is undergoing dialysis treatment.

In some embodiments, the therapeutically effective amount comprises about 1 to about 32 mg nalmefene or pharmaceutically acceptable nalmefene salt.

In some embodiments, the nalmefene or pharmaceutically acceptable nalmefene salt is administered to the subject 1 or 2 times per day. In some embodiments, about 1 to about 8 mg of the nalmefene or pharmaceutically acceptable nalmefene salt is administered to the subject once a day and is then titrated to an effective dose. In some embodiments, about 1 to about 8 mg of the nalmefene or pharmaceutically acceptable nalmefene salt is administered to the subject as an initial dose twice a day, and is then titrated to an effective dose of about 4 to about 32 mg. In some embodiments, the nalmefene or pharmaceutically acceptable nalmefene salt is administered as a first dose and a second dose within a 24-hour period and wherein the first dose is greater than the second dose or the second dose is greater than the first dose.

In some embodiments, the transmucosal administration is selected from buccal administration or sublingual administration. In some embodiments, the sublingual or buccal administration delivers about 1 to about 32 mg nalmefene or pharmaceutically acceptable nalmefene salt to the bloodstream of the subject in less than about 5, 30 or 60 minutes.

In some embodiments, the sublingual or buccal administration delivers about 1 to about 5 ng/mL nalmefene or pharmaceutically acceptable nalmefene salt to the bloodstream of the subject within about 5 minutes.

In some embodiments, the subject maximum blood concentration, $C_{max}$, of the nalmefene or pharmaceutically acceptable nalmefene salt after administration is about 1 to about 50 ng/mL.

In some embodiments, the subject blood AUC at time 0 to infinity after administration of the nalmefene or pharmaceutically acceptable nalmefene salt is about 5 to about 500 ng-hr/mL.

In some embodiments, the nalmefene or pharmaceutically acceptable nalmefene salt is configured in an immediate release transmucosal dosage form.

In some embodiments, the nalmefene or pharmaceutically acceptable nalmefene salt is at least about 50% dialyzable.

In some embodiments, the nalmefene or pharmaceutically acceptable nalmefene salt is administered through a single layer, self-supporting, mucoadhesive film. Particularly, the film comprises a first discrete domain comprising about 50-100 weight percent polymer matrix and about 0-50 weight percent of one or more of a permeation-enhancer, pH adjusting buffer, taste masking agent, and flavoring agent, based on the total weight of the first discrete domain. The film comprises a second discrete domain comprising the nalmefene or pharmaceutically acceptable nalmefene salt. In some embodiments, the second discrete domain is non-self-supporting.

In some embodiments, the subject is a human.

In some embodiments, the presently disclosed subject matter is directed to a single layer, self-supporting, mucoadhesive film. The film comprises a first discrete domain comprising about 50-100 weight percent polymer matrix and about 0-50 weight percent of one or more of a permeation-enhancer, pH adjusting buffer, taste masking agent, and flavoring agent, based on the total weight of the first discrete domain. The film further comprises a second discrete domain comprising the nalmefene or pharmaceutically acceptable nalmefene salt, wherein the second discrete domain is non-self-supporting.

In some embodiments, the nalmefene or pharmaceutically acceptable nalmefene salt is present as solid solution or a substantially-uniform, dispersed as a solid solution, amorphous or monomorphic crystalline microparticle residing on a surface of the first discrete domain.

In some embodiments, the nalmefene or pharmaceutically acceptable nalmefene salt has a dimension of less than about 25 μm, 10 μm, or 1 μm.

In some embodiments, the thickness of the first discrete domain is about 50%, 100%, 500%, 750%, 1000%, 2000%, 3000%, 4000%, 5000%, 7500% or 10000% of the thickness of second domain.

In some embodiments, the second discrete domain is physically inseparable from the first discrete domain.

In some embodiments, the first discrete domain is positioned directly adjacent to the second discrete domain.

In some embodiments, the local pH of the first discrete domain about 3.5 to about 8.5 and the local pH of the second discrete domain is 4 to 9, and the pH of the two domains are different.

In some embodiments, the polymer matrix is selected from water soluble, water swellable, and/or water erodible polymers.

In some embodiments, the second discrete domain further comprises about 0.1-50 weight percent of a self-aggregating moiety, a self-assembling moiety, or both, based on the total weight of the layer. In other embodiments, the self-aggregating and/or self-assembling moiety can be present in an amount of about 25-70 weight percent of the total weight of the second domain.

In some embodiments, the self-aggregating or self-assembling moieties are selected from one or more phospholipids, bile acids, bile salts, nanoplatelet structures, or edible clays.

In some embodiments, the ratio of pharmaceutical active to self-aggregating or self-assembling moieties is about 100:1 to about 1:10 by weight.

In some embodiments, the second domain further comprises about 0.1-5 weight percent of an oxygen scavenger.

In some embodiments, the second domain further comprises about 0.1-5 weight percent a drug solubilizer.

In some embodiments, the film is configured to provide directional delivery of the pharmaceutical active when placed in contact with the oral mucosa of a subject.

In some embodiments, the film further comprises one or more additional discrete domains, wherein said each of the additional discrete domains are substantially physically inseparable from the film device.

BRIEF DESCRIPTION OF THE DRAWINGS

The previous summary and the following detailed descriptions are to be read in view of the drawings, which illustrate some (but not all) embodiments of the presently disclosed subject matter.

DETAILED DESCRIPTION

Figure 1A:
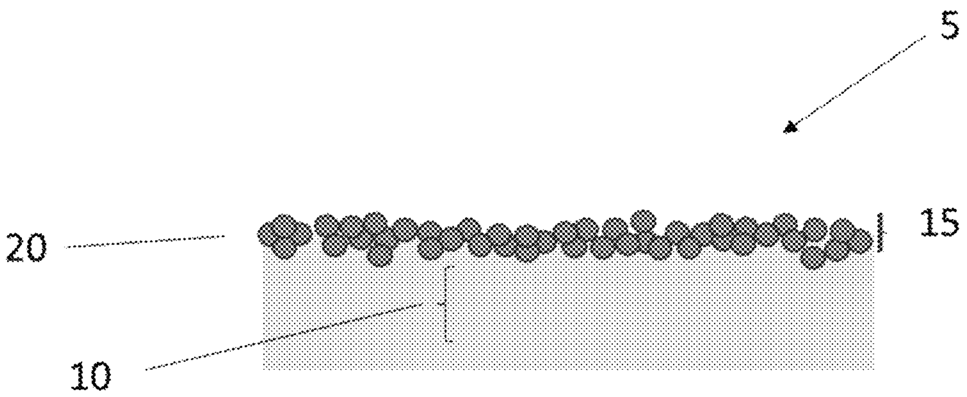
FIGS. 1*a*-1*e* are representations of transmucosal films comprising first and second discrete domains.

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a film" can include a plurality of such films, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

The presently disclosed subject matter is directed to an effective method of treating chronic kidney disease-associated pruritus. The term "chronic kidney disease" refers to a medical condition wherein a patient has either (i) a sustained reduction in GFR (glomerular filtration rate) of less than 60 mi/min per 1.73 $m^2$ of body surface for about 3 or more months, or (ii) a structural or functional abnormality of renal function for about 3 or more months, even in the absence of a reduced GFR. The term "pruritus" refers to an intense sensation of itching, commonly associated with chronic kidney disease. In some embodiments, the disclosed method includes transmucosally administering (e.g., across a mucosal tissue, such as buccal and/or sublingual tissues) nalmefene to a subject in need thereof.

In some embodiments, the transmucosal administration of nalmefene can treat chronic kidney disease-associated pruritus, as well as cholestatic pruritus and/or prurigo nodularis. Cholestatic pruritus is the sensation of itch to due liver disease. Cholestasis refers to the slowing or stopping of bile flow, which can be caused by any number of diseases of the liver (which produces bile), the gallbladder (which stores bile), or biliary tract (the conduit that allows the bile to leave the liver and gallbladder and enter the small intestine). When cholestasis occurs, conjugated bilirubin and associated waste products are deposited back into the bloodstream. The bile salts that deposit into the skin are believed to be responsible for the pruritus.

Prurigo nodularis is a skin disease characterised by pruritic (itchy) nodules that typically appear on the arms or legs of a subject. Patients often present with multiple excoriated lesions caused by scratching.

Substance P (SP) is a neuropeptide that plays a role in the induction and maintenance of pruritus. Since SP is expressed by NK-1 receptors on the pre-synaptic afferent, and KOR receptor at the post synaptic afferent, and both of the receptors are abundantly expressed in the skin and CNS, SP is therefore a logical target for novel anti-itch therapy. Without being bound by theory, it is believed that nalmefene works in multiple ways: 1) by blocking the expression of Substance P at the NK-1 receptor (antagonist) and/or 2) by blocking the pain signal to the CNS as a high affinity Kappa opioid (KOR) receptor. Without discrimination to either, pruritus is mitigated by either or both mechanisms of action.

The disclosed treatment method comprises transmucosally administering nalmefene to a subject with chronic kidney disease-related pruritus, cholestatic pruritus, and/or prurigo nodularis. The structure of nalmefene ($C_{21}H_{25}NO_3$, 6-methylene-6-deoxy-N-cyclopropylmethyl-14 hydroxydihydronormorphine) is shown below as Structure (I):

(I)

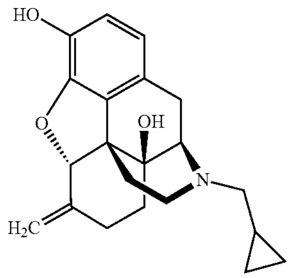

Nalmefene is a mixed mu-opioid receptor (MOR) antagonist and kappa-opioid receptor (KOR) agonist approved for use in the United States an antidote for opioid overdose[9]. Apart from its utility in antagonizing the sedation, respiratory depression, and other actions of opioid agents, nalmefene has also been found useful in treating diverse conditions such as hyperkinesia in children, senile dementia, and sudden infant death syndrome, among others. Oral administration of nalmefene has also been shown to be safe and effective for use in treating alcohol dependence.

As set forth above, nalmefene can be transmucosally administered to a subject to treat chronic kidney disease-associated pruritus, as well as cholestatic pruritus and/or prurigo nodularis. Transmucosal delivery refers to the delivery of a pharmaceutical agent across a mucous membrane in the oral cavity, pharyngeal cavity, or esophagus. Thus, the pharmaceutical agent is absorbed through the buccal, sublingual, gingival, pharyngeal, and/or esophageal mucosa. In some embodiments, the transmucosal administration of nalmefene is buccally or sublingually delivered. As used herein, "buccal" refers to administration directed towards the cheek, from within the mouth, through the mucosal membranes lining the cheeks (i.e., through the buccal mucosa). The term "sublingual" refers to administration beneath the tongue, through the mucosal membranes lining the floor of the mouth under the tongue (i.e., through the sublingual mucosa).

In some embodiments, the nalmefene can be formulated as a tablet (e.g., orally-dissolving tablet), liquid, gel, gum, disc, and/or an oral soluble film. However, oral administration of nalmefene can pose a serious safety risk to patients that have renal or hepatic impairment because of the inability of the kidney to remove its unwanted metabolites. For use in patients with end stage renal disease or liver failure, nalmefene can be delivered through a route of administration that avoids first pass metabolism. Particularly, avoiding first pass metabolism significantly reduces the oxidative glucuronide metabolite that must be reduced in impaired liver and kidney function.

For example, in some embodiments the nalmefene can be transmucosally delivered through the use of an oral film. The term "film" as used herein refers to a thin, flexible sheet of material and is intended to encompass coated films and film products. Particularly, an oral thin film comprising amorphous or crystalline nalmefene nano- and microparticles can be formulated. The term "nanoparticles" refers to nalmefene particles that are submicron in size. In some embodiments, the average longest dimension of a suitable nanoparticle is no greater than about 1,000 nanometers, 500 nanometers, 200 nanometers, 100 nanometers, 75 nanometers, 50 nanometers, 40 nanometers, 25 nanometers, or 20 nanometers. The term "crystalline" refers to a compound with a relatively well-defined crystal structure. The term "amorphous" refers to a compound in a non-crystalline state, without regions of crystallinity.

In some embodiments, the nalmefene nano- and microparticles reside in a discrete domain on the surface of an oral film. In some embodiments, the film can be a single layer film that includes two or more discrete domains, wherein at least one domain includes the nalmefene nano- and microparticles. As used herein the term "domain" refers to a region within a film that includes substantially different physical composition, chemical composition, and/or measurable physical properties (such as dissolution of the nalmefene, mucoadhesion, and/or moisture content) compared to another region of the film.

FIG. 1 illustrates one embodiment of single layer oral film 5 comprising a plurality of discrete domains, wherein at least one of the domains comprises nalmefene or a salt thereof. Particularly, film 5 comprises first domain 10 comprising one or more polymer matrices and second domain 15 comprising pharmaceutical active 20 (e.g., nalmefene or a salt thereof). In some embodiments, second domain 15 is not a self-supporting domain and cannot physically be separated from the first domain to maintain mechanical integrity. The term "non-self-supporting" describes a structure that cannot be physically separated to maintain mechanical integrity. Such domains can include (but are not limited to) extremely thin, fragile, discrete, and/or non-contiguous regions. In some embodiments, first domain 10 is self-supporting. In some embodiments, the first discrete domain is positioned adjacent or directly adjacent to the second discrete domain.

As used herein, the term "adjacent" refers to the positioning of two layers either in contact with each other directly or with another layer therebetween. The term "directly adjacent" refers to layers that are in contact with each other without any other layer therebetween.

First domain 10 can comprise one or more polymer matrices and optionally one or more permeation enhancers, pH adjusting buffers, taste masking agents, and/or flavors. Any desired polymer matrix can be used, including (but not limited to) water soluble, water swellable, and/or water erodible polymers. For example, in some embodiments, the polymer matrix can be selected from hydroxy propyl methyl cellulose (HPMC), methyl cellulose, hydroxyethyl cellulose (HPC), hydroxypropyl cellulose, polyvinyl pyrrolidone, sodium carboxymethyl cellulose, polyethylene oxide (PEO), pullulan, alginic acid, sodium alginate, polyethylene glycol, pectins, xanthan gum, tragancanth gum, guar gum, acacia gum, arabic gum, locust bean gum, gellan gum and combinations thereof, polyacrylic acid, Polycarbophil®, methyl methacrylate copolymer, carboxy vinyl copolymers, natural and hydrolyzed starch, gelatin type A and B, carrageenan, and combinations thereof.

As used herein the phrase "water soluble polymer" and variants thereof refer to a polymer that is at least partially soluble in water, fully or predominantly soluble in water, or absorbs water. Polymers that absorb water are often referred to as being water swellable polymers. In some embodiments, materials used in the polymer matrix of first domain 10 can be water soluble or water swellable at room temperature and/or other temperatures, such as temperatures exceeding room temperature.

In some embodiments, the polymer matrix can be present in an amount of about 5-100 weight percent of the total weight of the first domain (e.g., about 5, 10, 15, 20, 25, 30, 35, 40, 45, 50, 55, 60, 65, 70, 75, 80, 85, 90, 95, or 100 weight percent, based on the total weight of the domain). The polymer matrix provides a self-supporting structure and desired residence time for improved bioavailability.

The first domain can optionally include taste masking agents and/or flavoring agents to improve the flavor of the film. The term "taste masking agent" refers to an agent that is added to a composition to mask the taste of one or more unpleasant tasting components. The term "flavoring agent" refers to any additive that gives the disclosed film a desired taste or smell. Suitable taste masking agents can include (but are not limited to) cellulose acetate, cellulose acetate butyrate, ethylcellulose, methylcellulose, and combinations thereof. Suitable flavoring agents can include (but are not limited to) natural and artificial flavors such as oil of peppermint, menthol, oil of spearmint, vanilla, oil of cinnamon, oil of wintergreen, lemon oil, orange oil, grape oil, lime oil, grapefruit oil, apple flavor oil, raspberry oil, strawberry oil, pear oil, blueberry oil, blackberry oil, watermelon flavor, cherry oil, licorice oil, apricot essence, clove oil, anise oil, cardamom oil, coriander oil, *eucalyptus* oil, fennel oil, lemongrass oil, nutmeg oil, and combinations thereof. In some embodiments, the taste masking agents and/or flavoring agents can be present in an amount of about 0-5 weight percent of the total weight of the first domain (e.g., 0, 0.5, 1, 1.5, 2, 2.5, 3, 3.5, 4, 4.5, or 5 weight percent).

In some embodiments, the local pH of the first discrete domain is about 3.5 to about 8.5, such as about 3.5, 4, 4.5, 5, 5.5, 6, 6.5, 7, 7.5, 8, or 8.5. In some embodiments, the local pH of the second discrete domain is between 4 and 9, such as between 5 and 8, or between 6 and 7. In some embodiments, the pH of film 5 is between 3 and 9, such as between 4.5 and 7.5 or between 5 and 7.

In some embodiments, the second domain of film 5 comprises a therapeutically effective amount of nalmefene. The term "therapeutically effective amount" refers to the amount of pharmaceutical active that is effective at reducing, eliminating, treating, and/or controlling the symptoms of chronic kidney disease-associated pruritus, cholestatic pruritus, and/or prurigo nodularis. In some embodiments, the second domain of film 5 comprises about 1 to about 32 mg of nalmefene. Thus, film 5 can comprise at least about (or no more than about) 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 mg nalmefene.

Figure 1B:
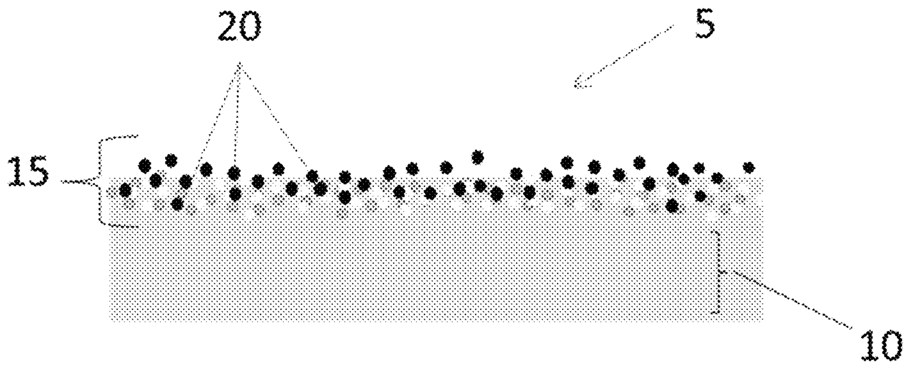

As shown in FIG. 1*b*, in some embodiments, second domain 15 can comprise a plurality of pharmaceutical actives 20. Thus, the film of FIG. 1*b* can include nalmefene and one or more additional compounds (e.g., NK-1 antagonist compounds). For example, in some embodiments, the disclosed film can include an effective dose of one or more pharmaceutical agents, such as (but not limited to) serlopitant ($C_{29}H_{28}F_7NO_2$). Serlopitant acts as a NK-1 receptor antagonist, and has the structure shown as Structure (II) below:

(II)

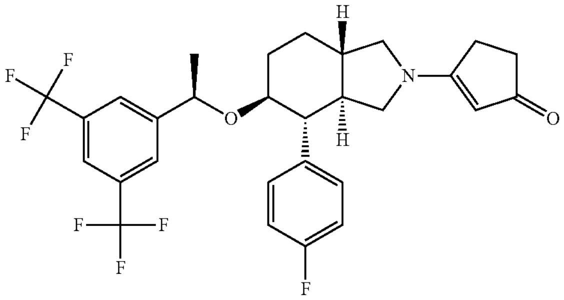

In some embodiments, the film 5 can comprise about 1 to about 32 mg of the additional pharmaceutical agent (e.g., serlopitant). Thus, the second active agent (or subsequent active agents) can be present in an amount of about 1-20 mg, 1-15 mg, 1-10 mg, or 1-5 mg.

In some embodiments, the second domain of film 5 can include a fixed drug ratio of nalmefene and serlopitant. For example, when combined, the fixed drug ratio can be about 1:10, 1:5, 1:4, 1:3, 1:2, 1:1, 2:1, 3:1, 4:1, 5:1, or 10:1 (nalmefene:serlopitant). However, film 5 is not limited and can include drug combinations with fixed drug ratios outside the ranges set forth above.

Figure 1C:
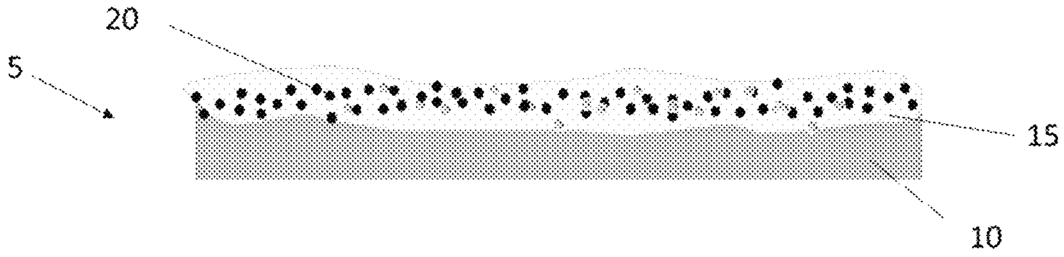
Figure 1D:
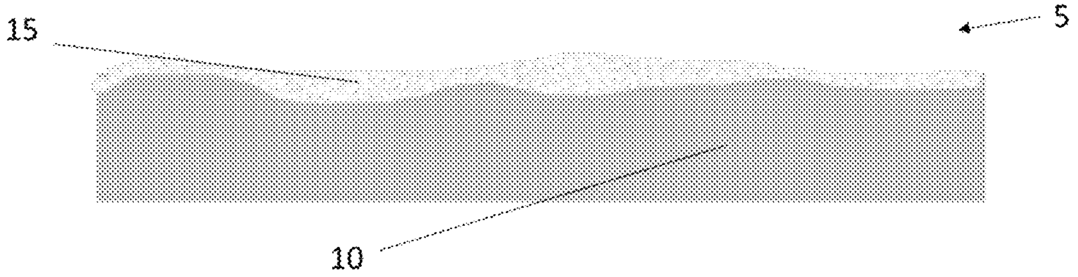
Figure 1E:
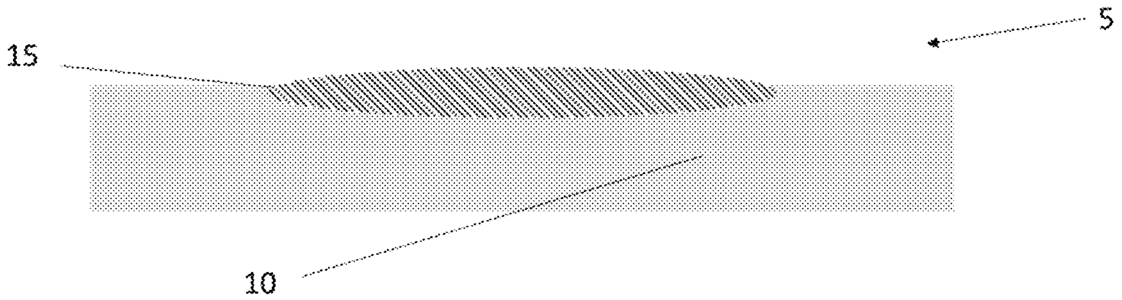

FIGS. 1*c*, 1*d* and 1*e* illustrate alternate embodiments of film 5 wherein pharmaceutical active 20 resides in second domain 15 configured as a barrier matrix on a surface of the first domain. As shown in FIG. 1*d*, second domain 15 can be substantially thinner compared to first domain 10, such as at least an order of magnitude thinner than the overall thickness of the film. For example, the thickness of first domain 10 can be about 500%, 750%, 1000%, 2000%, 3000%, 4000%, 5000%, 7500% or 10000% of the thickness of second domain 15. In some embodiments, the second domain of film 5 can be physically inseparable from the first domain. Similarly, for example, the surface area of first domain 10 can be about 100%, 150%, 200%, 250%, 300%, 350%, 400%, 450% or 500% of the surface area of second domain 15.

As shown in FIG. 1*c*, the second domain 15 can be about the same thickness as compared to first domain 10, such as the second domain is about 0-50% and the first domain is about 50-100% (or about 1:1) of the overall thickness of the film. For example, the thickness of the second domain 15 can be about 10%, 25%, 50%, 75%, or 90% of the thickness of first domain 10. In some embodiments, the second domain 15 of the film 5 can be physically inseparable from the first domain. Further, the surface area of the first domain 10 can be about 100%, 150%, 200%, 250%, 300%, 350%, 400%, 450% or 500% of the surface area of second domain 15, as shown in FIG. 1*e*.

In some embodiments, second discrete domain 15 can comprise one or more self-aggregating and/or self-assembling moieties that provide permeation enhancement characteristics. The term "self-assembling" as used herein refers to molecular structures that arrange themselves upon induced physical change and/or triggered phase transition to minimize the overall free energy of the device, resulting in a thermodynamically stable device. The term "self-aggregating" refers to a structure resulting from the ability of a molecule to aggregate into high concentration domains or "rich domains." In some embodiments, the self-aggregating and/or self-assembling moieties can be present in an amount of about 0-5 weight percent of the total weight of the second domain (e.g., 0, 0.5, 1, 1.5, 2, 2.5, 3, 3.5, 4, 4.5, or 5 weight percent). In other embodiments, the self-aggregating and/or self-assembling moiety can be present in an amount of about 25-75 weight percent of the total weight of the second domain (e.g., 25, 30, 35, 40, 45, 50, 55, 60, 65, 70, or 75 weight percent). The self-aggregating and/or self-assembling moieties provide directional permeation.

In some embodiments, suitable self-aggregating and/or self-assembling moieties can include (but are not limited to) phospholipids, bile salts, nanoplatelets, clays, polar lipids, or combinations thereof. Suitable examples of the self-aggregating and/or self-assembling moieties can include phosphatidylcholine, phosphatidic acid, phosphatidylcholine, phosphatidylethanolamine, phosphatidylglycerol, phosphatidylcholine, phosphatidylserine, phosphatidylinositol, phosphatidylinositol phosphate, phosphatidylinositol bisphosphate, phosphatidylinositol triphosphate, and/or sphingomyelin. More specifically, the self-aggregating and/or self-assembling moieties can comprise 1,2-didecanoyl-sn-glycero-3-phosphocholine, 1,2-dierucoyl-sn-glycero-3-phosphate (sodium salt), 1,2-dierucoyl-sn-glycero-3-phosphocholine, 1,2-dierucoyl-sn-glycero-3-phosphoethanolamine, 1,2-dierucoyl-sn-glycero-3 [phospho-rac-(1-glycerol . . . ) (sodium salt), 1,2-dilinoleoyl-sn-glycero-3-phosphocholine, 1,2-dilauroyl-sn-glycero-3-phosphate (sodium salt), 1,2-dilauroyl-sn-glycero-3-phosphocholine, 1,2-dilauroyl-sn-glycero-3-phosphoethanolamine, 1,2-dilauroyl-sn-glycero-3 [pPhospho-rac-(1-glycerol) (sodium salt), 1,2-dilauroyl-sn-glycero-3[phospho-rac-(1-glycerol) (ammonium salt), 1,2-dilauroyl-sn-glycero-3-phosphoserine (sodium salt), 1,2-dimyristoyl-sn-glycero-3-phosphate (sodium salt),1,2-dimyristoyl-sn-glycero-3-phosphocholine,1,2-dimyristoyl-sn-glycero-3-phosphoethanolamine,1,2-dimyristoyl-sn-glycero-3[phospho-rac-(1 glycerol . . . ) (sodium salt),1,2-dimyristoyl-sn-glycero-3[phospho-rac-(1-glycerol . . . ) (ammonium salt), 1,2-dimyristoyl-sn-glycero-3[phospho-rac-(1-glycerol . . . ) (sodium/ammonium salt), 1,2-dimyristoyl-sn-glycero-3-phosphoserine (sodium salt), 1,2-dioleoyl-sn-glycero-3-phosphate (sodium salt), 1,2-dioleoyl-sn-glycero-3-phosphocholine, 1,2-dioleoyl-sn-glycero-3-phosphoethanolamine, 1,2-dioleoyl-sn-glycero-3[phospho-rac-(1-glycerol . . . ) (sodium salt), 1,2-dioleoyl-sn-glycero-3-phosphoserine (sodium salt), 1,2-dipalmitoyl-sn-glycero-3-phosphate (sodium salt), 1,2-dipalmitoyl-sn-glycero-3-phosphocholine, 1,2-dipalmitoyl-sn-glycero-3-phosphoethanolamine, 1,2-dipalmitoyl-sn-glycero-3 [phospho-rac-(1-glycerol.) (sodium salt), 1,2-dipalmitoyl-sn-glycero-3[phospho-rac-(1-glycerol) (ammonium salt), 1,2-dipalmitoyl-sn-glycero-3-phosphoserine (sodium salt), 1,2-distearoyl-sn-glycero-3-phosphate (sodium salt), 1,2-distearoyl-sn-glycero-3-phosphocholine,1,2-distearoyl-sn-glycero-3-phosphoethanolamine, 1,2-distearoyl-sn-glycero-3[phospho-rac-(1-glycerol . . . ) (sodium salt), 1,2-distearoyl-sn-glycero-3[phospho-rac-(1-glycerol) ammonium salt), 1,2-distearoyl-sn-glycero-3-phosphoserine (sodium salt), hydrogenated egg PC hydrogenated soy PC, 1-myristoyl-sn-glycero-3-phosphocholine, 1-palmitoyl-sn-glycero-3-phosphocholine, 1-stearoyl-sn-glycero-3-phosphocholine, 1-myristoyl-2-palmitoyl-sn-glycero 3-phosphocholine, 1-myristoyl-2-stearoyl-sn-glycero-3-phosphocholine, 1-palmitoyl-2-myristoyl-sn-glycero-3-phosphocholine, 1-palmitoyl-2-oleoyl-sn-glycero-3-phosphocholine,1-palmitoyl-2-oleoyl-sn-glycero-3-phosphoethanolamine, 1-palmitoyl-2-oleoyl-sn-glycero-3 [phospho-rac-(1-glycerol)] (sodium salt), 1-palmitoyl-2-stearoyl-sn-glycero-3-phosphocholine, 1-stearoyl-2-myristoyl-sn-glycero-3-phosphocholine, 1-stearoyl-2-oleoyl-sn-glycero-3-phosphocholine, 1-stearoyl-2-palmitoyl-sn-glycero-3-phosphocholine, 1-stearoyl-2-palmitoyl-sn-glycero-3-phosphocholine; edible clay components such as sodium bentonite, polyphosphate, montmorillonite, kaolin, cloisite; bile acids and salts that include cholic acid, sodium and calcium cholates salts, chenodeoxycholic acid, sodium and calcium chenodeoxycholates salts, chenodeoxycholic acid, sodium and calcium chenodeoxycholates salts, glycocholic acid, sodium and calcium glycocholates salts, glycyrrhetinic acid, glycyrrhentinate sodium, taurocholic acid, sodium and calcium taurocholates salts, lithocholic acid, sodium and calcium lithocholates salts; nanoplatelets, bentonite, cloisite, and/or combinations thereof.

In some embodiments, second domain 15 can optionally comprise one or more oxygen scavengers. The term "oxygen scavenger" as used herein refers to a composition that reduces or eliminates the generation of unwanted oxidation products. In some embodiments, the oxygen scavenger is effective to absorb oxygen. Suitable oxygen scavengers that can be incorporated into second domain 15 can include (but are not limited to) ascorbates, isoascorbates, tannins, sulfites, oxidizable polymers, polyacids, polynucleic acids, proteins, polysaccharides, polypeptides, ethylenediamine tetraacetic acid (EDTA) and salts thereof, organic glutamic acid and salts thereof, citric acid and salts thereof, phosphonates, histidine, phytochelatin, hemoglobin, chlorophyll, humic acid, transferrin, desferrioxamine, vitamin E acetate, tocopherol, and combinations thereof. In some embodiments, the oxygen scavenger can be present in an amount of about 0-5 weight percent of the total weight of the second domain (e.g., 0, 0.5, 1, 1.5, 2, 2.5, 3, 3.5, 4, 4.5, or 5 weight percent).

In some embodiments, the first and/or second domains of film 5 can comprise one or more bioenhancers, pH control elements, solubility enhancers, and/or solvents to maximize absorption through the oral mucosa of a subject. The term "bioenhancer" refers to a substance that increases the bioactivity, bioavailability, and/or efficacy of nalmefene. Suitable bioenhancers can include (but are not limited to) one or more fatty acids, alkaloids, Piperine, allicin, curcumin, quercetin, and the like. In some embodiments, the bioenhancer can be present in an amount of about 0-5 weight percent of the total weight of the first domain (e.g., 0, 0.5, 1, 1.5, 2, 2.5, 3, 3.5, 4, 4.5, or 5 weight percent).

The term "pH control element" refers to any element (such as a buffer) that can resist a change in pH. For example, in some embodiments, the pH control element can be selected from one or more of phosphate, acetate, citrate, arginine, TRIS, or histidine buffers. In some embodiments, the pH control element can be present in an amount of about 0-5 weight percent of the total weight of the first domain (e.g., 0, 0.5, 1, 1.5, 2, 2.5, 3, 3.5, 4, 4.5, or 5 weight percent).

The term "solubility enhancer" refers to an agent that forms a solubilized phase of a pharmaceutical active (e.g., nalmefene). Suitable drug solubilizers can include (but are not limited to) solvents, oils, surfactants, and/or phospholipids. In some embodiments, the drug solubilizer can be present in an amount of about 0-5 weight percent of the total weight of the second domain (e.g., 0, 0.5, 1, 1.5, 2, 2.5, 3, 3.5, 4, 4.5, or 5 weight percent).

The term "solvent" refers to a substance that dissolves a solute. Suitable solvents can include (but are not limited to) water, alcohol, polyol, or combinations thereof. In some embodiments, the solvent can be present in an amount of about 0-5 weight percent of the total weight of the first domain (e.g., 0, 0.5, 1, 1.5, 2, 2.5, 3, 3.5, 4, 4.5, or 5 weight percent).

In some embodiments, film 5 can include more than 2 discrete domains. For example, the disclosed film can include a first discrete domain comprising a film-forming polymeric matrix and optionally one or more pH adjusting buffer, taste masking agent, and/or flavor to provide effective taste masking and/or directional permeation. The film can include a second discrete domain comprising a self-assembling phospholipid and/or bile salts to provide permeation enhancement. The film can further comprise a third discrete domain that includes at least one pharmaceutical active or its salts thereof and optionally a mucoadhesive polymer, pH adjusting buffer, and/or oxygen scavenger to provide mucoadhesion and/or a high driving force resulting from a high concentration microenvironment when placed in contact with the oral mucosa.

In some embodiments, film 5 can be a mucoadhesive film. The term "mucoadhesive" as used herein refers to the attachment of synthetic or natural polymers to a biological substrate, as defined by Robinson, J R, "Rationale of Bioadhesion/mucoadhesion", in Gurny R., Junginger H. E. eds. Bioadhesion: Possibilities and Future Trends, Stuttgart: Wissenschaftliche Verlagsesellschaft, Stuttgart, pages Vol. 13 page 15 (1990), the entire content of which is incorporated by reference herein. There is currently no known single-layer film structure that comprises a plurality of discrete domains, wherein at least one of the domains is rich in pharmaceutical active, and at least one discrete domain provides effective taste masking and enhanced transmucosal absorption when the discrete domain comprising the pharmaceutical active is placed in contact with the oral mucosa. In some embodiments, at least one discrete domain provides enhanced transmucosal absorption. In some embodiments, the mucoadhesive polymer provides enhanced absorption when the first discrete domain is placed in contact with the mucosa tissue of a subject.

As set forth above, film 5 is a single layer film. The term "single layer" refers to a structure that does not include layers that can easily be separated from each other, such as by peeling apart or wedging the regions away from each other. Thus, the disclosed film includes a single layer with two or more domains, but is not a multi-layered, laminated structure. It should be appreciated that domains 10, 15 can be discrete or contiguous in structure, unlike a layer that must be contiguous. In some embodiments, the disclosed single layer film comprises at least one domain with a thickness of no more than 500 μm in an unhydrated state. In some embodiments, each domain in film 5 has a thickness of 500 μm or less.

The presently disclosed subject matter further comprises method of forming a continuous and uniform single layer film product comprising first domain and second discrete domains, wherein said first and second discrete domains are substantially inseparable and have different concentrations of the pharmaceutical active. For example, in some embodiments, the disclosed films can be constructed by preparing a first domain comprising a wet polymer matrix and optionally one of more of a permeation enhancer, pH adjusting buffer, taste masking agent, and/or flavor agent using a first solvent. The first wet film is formed by casting the first wet polymer matrix. A drying apparatus can be used to dry the wet polymer matrix and expose the wet film to a temperature sufficient to flash off the first solvent and thereby dry the film as a continuous single layer film laminate. A second wet solution or suspension comprising a pharmaceutical active (e.g., nalmefene) can then be prepared using a second solvent. A predetermined amount of the second wet solution is deposited via spraying, electro-spraying, atomized coating, and/or ultra-thin web-coating processes onto selected areas on a surface of the first dry film to form a wet multi-domain film. The film is then dried in a drying apparatus and exposed to a temperature sufficient to flash off the second solvent to form a dry continuous single layer film laminate comprising first and second discrete domains. In some embodiments, the temperature can range from about room temperature to about 250° C.

In embodiments where film 5 is a transmucosal single layer film device, the film can be prepared by procuring a dry, drug-free web-coated polymer matrix laminate roll from a suitable vendor (such as Lohmann Therapie Systeme (LTS), Tapemark Inc, Aquestive Therapeutics, or ARx LLC). The second wet solution or suspension comprising a pharmaceutical active can then be prepared using a second solvent. A predetermined amount of the second wet solution or suspension can be deposited onto selected areas of the surface of the first dry film by spraying, electro-spraying, atomized coating, and/or ultra-thin web-coating processes. The wet multi-domain film can then be deposited in a drying apparatus and exposed to a temperature sufficient to flash off the second solvent (e.g., about room temp to 250° C.) to form a dry continuous single layer film laminate comprising first and second discrete domains. In some embodiments, the second discrete domain comprising the pharmaceutical active is substantially thinner than the polymer-comprising first discrete domain.

In some embodiments, transmucosal single layer film device 5 can be constructed by preparing a first wet polymer matrix and one or more of a permeation enhancer, pH adjusting buffer, taste masking agent, and/or a flavor using a first solvent. A first wet film can be formed by casting the wet polymer matrix. A second wet solution or suspension comprising pharmaceutical active 20 (or a salt thereof) and an oxygen scavenger and/or a drug solubilizer can be prepared in a second solvent. A predetermined amount of the second wet solution or suspension can then be deposited on a surface of the first wet film to form a wet multi-domain film using spraying, electro-spraying, atomized coating, and/or ultra-thin web-coating processes. The wet multi-domain film can be deposited in a drying apparatus and exposed to a temperature sufficient to flash off the first and second solvents (e.g., about room temp to 250° C.) to form single layer transmucosal film device comprising a first and second discrete domains. In some embodiments, the second discrete domain is substantially thinner than the first discrete domain.

In some embodiments, transmucosal single layer film device 5 can be constructed by preparing a first wet polymer matrix and one or more of a permeation enhancer, pH adjusting buffer, taste masking agent, self-aggregating moiety (such as bentonite) and/or a flavor using a first solvent. A first wet film can be formed by casting the wet polymer matrix. The first wet polymer matrix can be deposited a dryer apparatus and exposed to a temperature sufficient to flash off the first solvent to form a first dry film cast as a continuous single layer film laminate. A second wet solution or suspension comprising pharmaceutical active 20 (or a salt thereof) and optionally an oxygen scavenger and/or a drug solubilizer (such as a self-assembling phospholipid and/or bile salts) can then be prepared in a second solvent. A predetermined amount of the second wet solution or suspension can be deposited on a surface (or onto selected areas of a surface) of the first dry film using spraying, electrospraying, atomized coating, and/or ultra-thin web-coating processes. The wet multi-domain film can be deposited in a drying apparatus and exposed to a temperature sufficient to flash off the first and/or second solvents (e.g., about room temp to 250° C.) to form a dry continuous single layer film laminate comprising a first and second discrete domains. In some embodiments, the second discrete domain is substantially thinner than the first discrete domain.

Film 5 can be configured in any desired form, such as (but not limited to) film strips, sheets, discs, wafers, and the like. The disclosed film can have any desired thickness, such as about 50 to about 500 μm, although films with greater or lesser thicknesses are included within the scope of the presently disclosed subject matter. Film 5 can be configured in any desired shape, such as rectangular, square, rounded, triangular, abstract, and the like. It should be appreciated that film 5 can have any desired thickness and/or size suitable for the intended use. For example, the film can be a single-dosage sized unit that is to be placed into the oral cavity of the user.

Film 5 can be formed from a continuous roll of film or can be sized to a desired length and width.

In use, the disclosed film comprising the pharmaceutical active (e.g., nalmefene) is placed under the tongue of a subject (e.g., in the sublingual or buccal space). The film rapidly sticks, disintegrates, and dissolves, allowing the pharmaceutical active to dissolve and subsequently be absorbed directly into the bloodstream. As set forth above, nalmefene is a KOR agonist and an NK-1 receptor antagonist. In this way, the expression of SP is believed to be reduced at the pre-synaptic afferent, while blocking the itch signal as a KOR agonist. Therefore, administering nalmefene to bind the NK-1 receptor modifies (e.g., reduces or inhibits) expression of SP and blocks the itch signal transmission to the CNS, which has been linked to pruritus.

The pharmaceutical active resides at a high concentration in a molecular state in the microenvironment in immediate proximity to the subject's mucosa when administered. In this way, rapid transmucosal absorption of the pharmaceutical active is provided. In some embodiments, the rate of dissolution of the pharmaceutical active is significantly faster than the dissolution rate of the matrix.

In some embodiments, film 5 can be administered about 1-2 times per day to a subject in need thereof. However, it should be appreciated that dosage can depend on many factors, such as severity of the condition, concentration of the nalmefene, weight of the subject, etc. The term "subject" as used herein refers to an animal, including primates (monkey, ape, human, etc.) or non-primate (cow, horse, pig, cat, dog, rat, mouse, bird, fish, etc.).

The transmucosal film can be administered buccally or sublingually to deliver about 1-32 mg of nalmefene to the subject. For example, in some embodiments, the nalmefene can be transmucosally administered at an initial dose of about 1-5 mg once or twice a day and then titrated to an effective dose (such as about 5-32 mg). In some embodiments, the nalmefene can be transmucosally administered with a first dosage at a first timepoint (e.g., in the morning) and a second dosage at a second timepoint (e.g., in the afternoon), wherein the first and second doses are equal or unequal.

In some embodiments, the nalmefene is in an immediate release transmucosal dosage form and administered through the buccal or sublingual route that provides in the patient a mean $C_{max}$ of from about 1-50 ng/mL. "$C_{max}$" refers to the maximum plasma, serum, or blood concentration of a drug (e.g., nalmefene or a pharmaceutically acceptable salt thereof) following administration. For example, the sublingual or buccal administration can deliver about 1-5 ng/mL nalmefene or pharmaceutically acceptable nalmefene salt to the bloodstream of the subject within about 5 minutes.

In some embodiments, the nalmefene is in an immediate release transmucosal dosage form and is administered buccally or sublingually and provides in the subject a mean $AUC_{0\text{-}infinity}$ of from about 5-500 ng-hr/mL. "AUC" refers to the area under the time/plasma concentration curve after the administration of a pharmaceutical composition. "$AUC_{0\text{-}infinity}$" denotes the area under the plasma concentration curve from time 0 to infinity.

In some embodiments, the subject has chronic kidney-disease related pruritus, cholestatic pruritus, and/or prurigo nodularis. In some embodiments, the subject is under dialysis treatment. As is well known in the art, dialysis is a process for blood purification of subjects with acute or chronic renal insufficiency. In some embodiments, the subject has chronic kidney disease or a reduced renal function. The nalmefene and/or nalmefene glucuronide can be at least about 50% dialyzable when the patient is under the treatment of dialysis (e.g., at least 50, 60, 70, 80, 90, or 100 percent dialyzable). "Dialyzable" refers to molecules that are able to pass through a dialysis membrane (i.e., a semi-permeable membrane).

The disclosed film can therefore be used to treat chronic kidney disease-associated pruritus, cholestatic pruritus, and/or prurigo nodularis in a subject. To date, no oral transmucosal formulations of nalmefene exist for the treatment of these conditions. As a result, the presently disclosed subject matter provides life-changing relief to afflicted patients.

Due at least in part to the safe pharmacology of nalmefene and/or the suitable oral transmucosal route of administration, nalmefene has the potential to be the standard-of-care for the treatment of chronic pruritus, chronic kidney disease associated pruritus, and cholestatic pruritus.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Injection of SP in Mice

The method of treatment of pruritus was established using C57BL mice where substance P (SP) induced pruritus was created to induce the disease state. The C57BL mouse and ICR mouse model are well-established and validated pruritogenic model and have been successful used in the demonstration of pruritogenic pharmacodynamics when intradermally-induced with SP.

Healthy male C57BL/6 mice ~6-8 weeks of age and ranging from 21.2 to 26.8 grams in weight at study initiation were used in the Examples. The mice were acclimated for a minimum of 5 days prior to the beginning of the study. The mice were identified by tail mark and cage label. The study was not blinded. Mice were fed species-specific food, and food and water were supplied ad libitum to the animals.

Figure 2A:
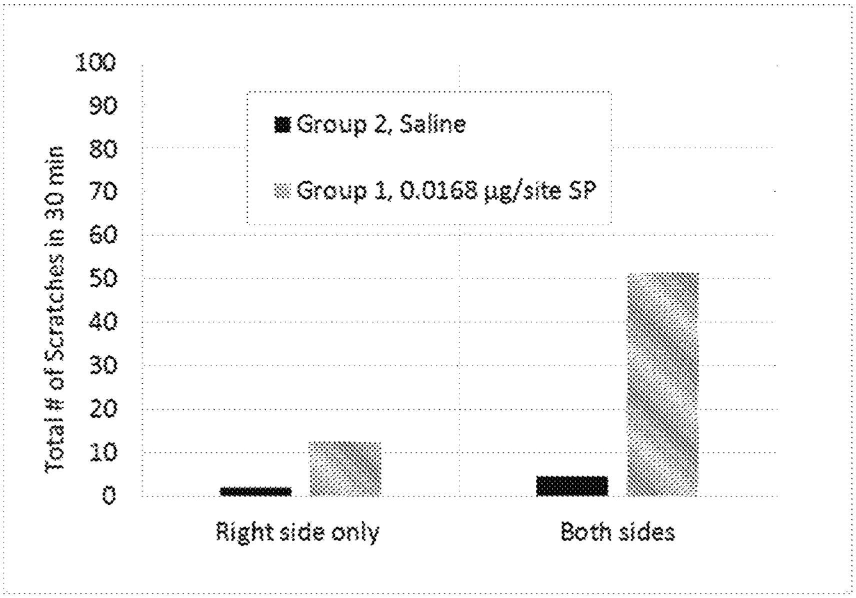
FIG. 2*a* is a bar graph illustrating the total number of scratches in mice injected with SP (Group 1) and saline (Group 2).

Male C57BL mice were given an intradermal (ID) injection of 0.0168 μg of SP (N=4, Group 1) or PBS (N=2, Group 2) on either the right side only or on both sides. Scratching behavior at the injection site was monitored for 30 minutes from time of injection by two separate observers. As shown in FIG. 2*a*, local site scratching behavior was more frequent in mice injected with SP than in PBS-injected mice, demonstrating that SP injection effectively induced pruritus.

Figure 2B:
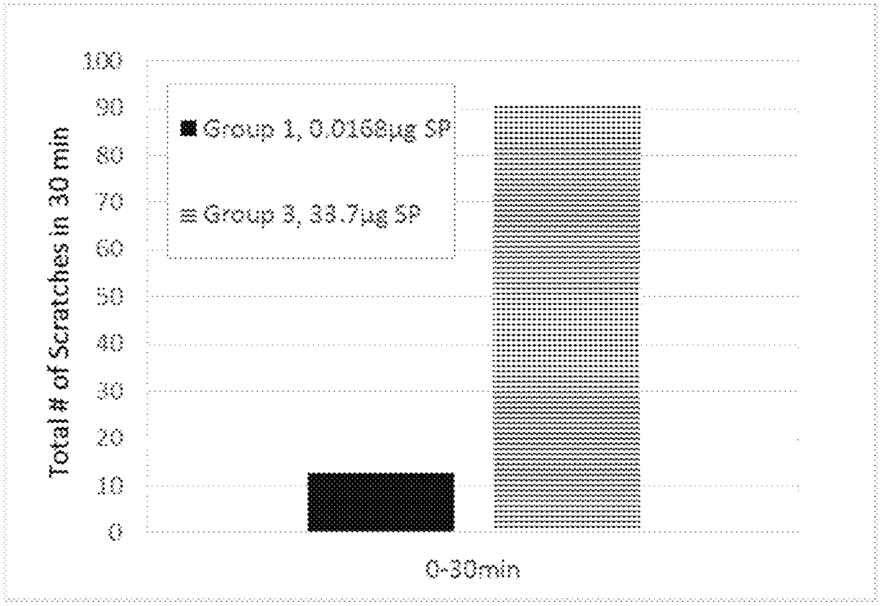
FIG. 2*b* is a bar graph illustrating the total number of scratches in mice injected with low and high concentrations of SP (Groups 1 and 3).

The original dose of 0.0168 μg SP (Group 1) was compared to a higher dose of 33.7 μg SP (N=4, Group 3). As shown in FIG. 2*b*, a higher dose of SP correlated to increased scratching in mice compared to the lower dosage. It was therefore concluded that the scratching behavior was a direct response to the presence and amount of SP.

Example 2

Injection of SP and Nalmefene in Mice I

To test the effect of nalmefene on SP-induced scratching behavior, a dose of nalmefene was given via subcutaneous (SC) injection mimicking 100% bioavailability 1 hour prior to SP ID injection at 33.7 μg in male C57BL mice (N=5, Group 4). Scratching behavior was monitored for 30 and 60 minutes after SP injection. Controls included mice that received PBS instead of SP (N=6, Group 5) and mice that received a placebo dose of PBS and ID dose of SP (N=4, Group 6).

Figure 3:
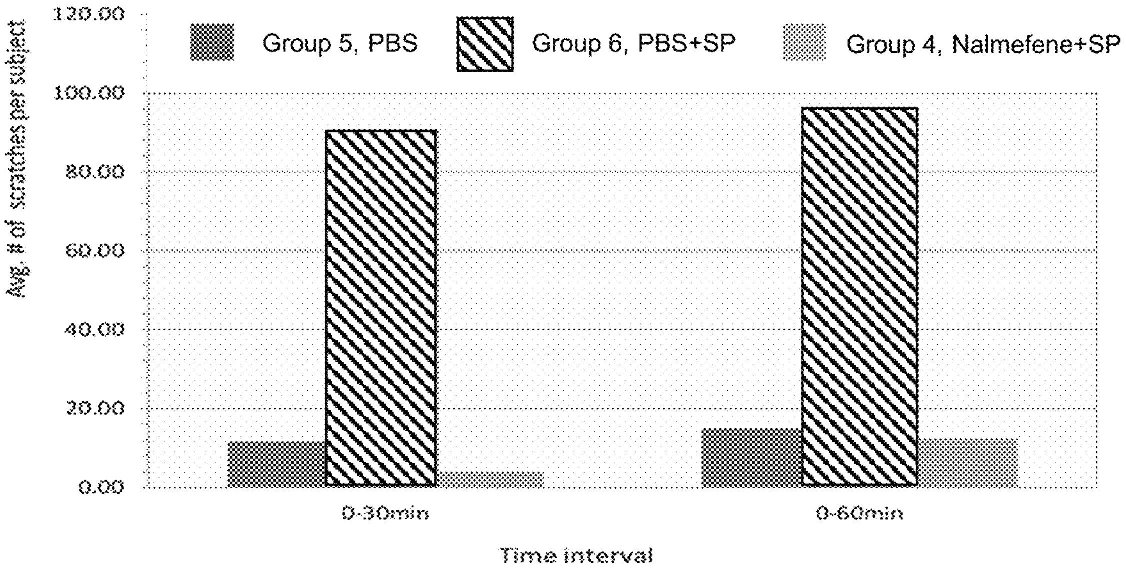
FIG. 3 is a bar graph illustrating the average number of scratches per mouse after the administration of PBS (Group 5), PBS and SP (Group 6), or nalmefene and SP (Group 4) at 0-30 and 0-60 minute timepoints.

As shown in FIG. 3, nalmefene completely mitigated the pruritogenic response to SP.

Example 3

Injection of SP and Nalmefene in Mice II

Male C57BL mice were dosed with SP or nalmefene as follows: Group 7 (N=4) received SP in sodium acetate at a dose of 250 nM/50 μL. Group 8 (N=4) received SP in phosphate buffered saline (PBS) at a dose of 250 nM/50 μL. Group 9 (N=4) received SP in PBS at a dose of 0.5 mM/50 μL. Various scratching behavior was video recorded and assessed.

Fifteen male C57BL/6 mice received a single intradermal (ID) bolus injection of substance P (SP) or PBS. Group 10 (N=6) received a single 50 μL injection of PBS. Group 11 (N=4) received SP in PBS at a dose of 0.5 mM/50 μl. Group 12 (N=5) received nalmefene 0.075 mg/75 μL subcutaneous (SC) 30 minutes prior to SP in PBS at a dose of 0.5 mM/50 μL. Scratching behavior was video recorded and assessed.

In-life dosing for each group was then conducted according to the following procedures:

Group 7: All mice were placed in a clear cylindrical enclosure 30 minutes prior to testing to acclimate. An ID bolus injection of SP in sodium acetate was administered.

Groups 8 and 9: All mice were placed in a clear cylindrical enclosure 30 minutes prior to testing to acclimate. An ID bolus injection of SP in PBS was administered. Recording began immediately following injection of SP and recorded for 30 minutes.

Groups 10 and 11: All mice were placed in a clear cylindrical enclosure 60 minutes prior to testing to acclimate. An ID bolus injection of SP in PBS was administered. Recording began immediately following injection of SP and recorded for 60 minutes.

Group 12: All mice were placed in clear cylinder enclosures for 60 minutes prior to testing to acclimate. A SC bolus injection of nalmefene was administered. 30 minutes after the nalmefene injection, an ID bolus injection of SP in PBS was administered. Recording began immediately following injection of SP and recorded for 60 minutes.

A summary of the study design is set forth below in Table 1.

TABLE 1

SP, Nalmefene Injection Dosing

| Dose Group | N= | Dosing Route | Test article | Vehicle | Dose (mg) | Dose Vol. (mL) | Dosing Conc. (mg/mL) | Itching Assessment Observation |
|---|---|---|---|---|---|---|---|---|
| 7 | 4 | ID | SP (T0 min) | Na acetate | 0.00001685 | 0.05 | 0.000337 (250 mM) | T0-T30 |
| 8 | 4 | ID | SP (T0 min) | PBS | 0.00001685 | 0.05 | 0.000337 (250 mM) | |
| 9 | 4 | ID | SP (T0 min) | PBS | 0.0337 | 0.05 | 0.674 (0.5 mM) | |
| 10 | 6 | ID | PBS (T0 min) | n/a | n/a | 0.05 | n/a | T0-T60 |
| 11 | 4 | ID | SP (T0 min) | PBS | 0.0337 | 0.05 | 0.674 (0.5 mM) | |

TABLE 1-continued

| SP, Nalmefene Injection Dosing | | | | | | | | |
|---|---|---|---|---|---|---|---|---|
| Dose Group | N= | Dosing Route | Test article | Vehicle | Dose (mg) | Dose Vol. (mL) | Dosing Conc. (mg/mL) | Itching Assessment Observation |
| 12 | 6 | SC | Nalmefene (T-30 min) | PBS | 0.075 | 0.075 | 1 | |
| | | ID | SP (T0 min) | PBS | 0.0337 | 0.05 | 0.674 (0.5 mM) | |

Animals in Groups 7-9 were acclimated for 1 hour prior to recording. Behavioral recording lasted for 30 minutes (T0-T30).

Animals in Groups 10-12 were acclimated for 1 hour prior to recording. Behavioral recording lasted for 60 minutes (T0-T60). 6 animals were dosed for Group 12 but only 5 animals were tested due to one animal being excluded as an outlier due to no response to SP injection.

The number of scratches per 0-30 minutes for Groups 7-9 is given below in Table 2. The numbers for Groups 7 and 8 were averaged together.

Figure 4:
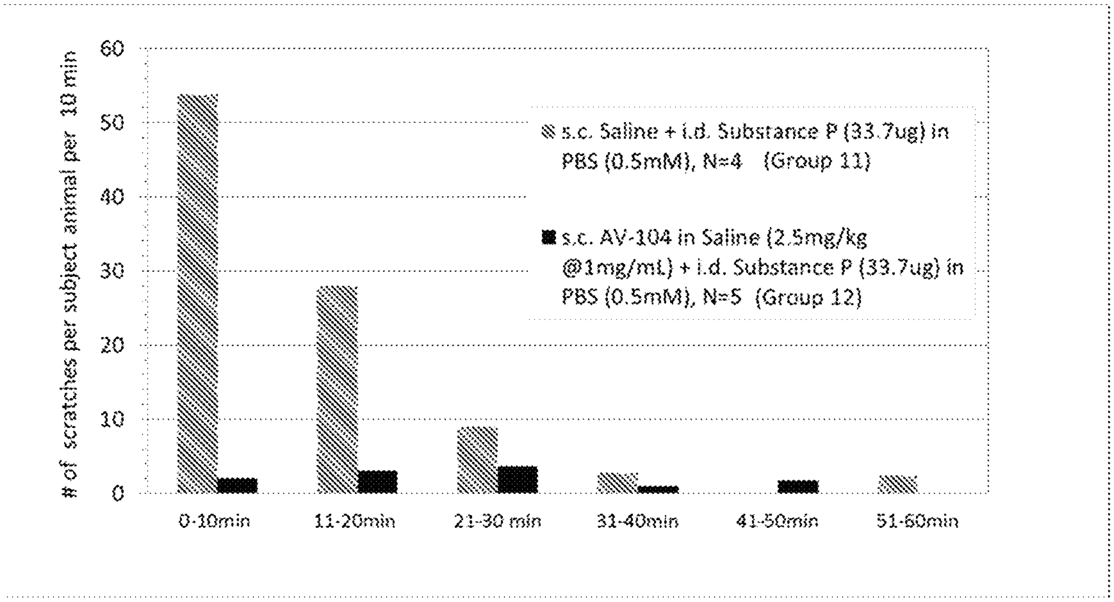
FIG. 4 is a bar graph illustrating the number of scratches per mouse after injection of PBS (Group 10), 0.5 mM SP (Group 11), or 0.75 mg nalmefene (Group 12) at 10 minute intervals.

The number of scratches per 10-minute time interval for Groups 10-12 is given below in Table 3. The data is also shown graphically in FIG. 4.

TABLE 2

| Scratches, Groups 7-9, 0-30 Minutes | | | | | |
|---|---|---|---|---|---|
| Animal No. | 1 | 2 | 3 | 4 | Avg. |
| 250 mM SP | | | | | |
| Rt. Side | 0 | 36 | 4 | 10 | 12.5 |
| Left Side | 1 | 69 | 4 | 82 | 39 |
| Facial | 110 | 139 | 137 | 54 | 110 |
| Other | 38 | 45 | 43 | 26 | 38 |
| SP 0.5 mM | | | | | |
| Rt. Side | 28 | 7 | 13 | 19 | 16.75 |
| Left Side | 15 | 22 | 11 | 0 | 12 |
| Facial | 5 | 20 | 48 | 46 | 29.75 |
| Other | 7 | 27 | 35 | 15 | 21 |

TABLE 3

| Scratches, Groups 10-12 | | | | | | | |
|---|---|---|---|---|---|---|---|
| | No. | 0-10 min | 10-20 min | 20-30 min | 30-40 min | 40-50 min | 50-60 min |
| Group 10 PBS | 1 | 5 | 1 | 0 | 1 | 0.5 | 0 |
| | 2 | 6 | 32 | 36 | 17 | 5.5 | 0 |
| | 3 | 20 | 34.5 | 23 | 3.5 | .5 | 7 |
| | 4 | 9.5 | 26 | 5.5 | 6.5 | 0 | 0 |
| | 5 | 0.5 | 0 | 2.5 | 0 | 0 | 0 |
| | 6 | 0 | 11.5 | 0 | 0 | 3.5 | 0 |
| | Avg. | 6.83 | 17.5 | 11.17 | 4.67 | 2 | 1.17 |
| | Std. Dev. | 7.02 | 14.68 | 14.23 | 6.24 | 2.13 | 2.72 |
| Group 11, SP 0.5 mM | 1 | 57.5 | 41.5 | 20 | 15.5 | 0 | 4 |
| | 2 | 66 | 1 | 0 | 0 | 0 | 5.5 |
| | 3 | 49 | 45 | 0.5 | 2.5 | 0 | 0 |
| | 4 | 42.5 | 24.5 | 2.5 | 6 | 0 | 0 |
| | Avg. | 53.75 | 28 | 5.75 | 6 | 0 | 2.38 |
| | Std. Dev. | 9.46 | 18.61 | 8.85 | 6.29 | 0 | 2.6 |
| Group 12, Nalmefene + SP | 1 | 10 | 0 | 0 | 0 | 0.5 | 0.5 |
| | 2 | 0 | 13 | 16 | 0 | 5 | 0 |
| | 3 | 0 | 0 | 0 | 0 | 0 | 0 |
| | 4 | 0 | 0 | 0 | 0 | 0 | 0 |

TABLE 3-continued

| Scratches, Groups 10-12 | | | | | | |
|---|---|---|---|---|---|---|
| No. | 0-10 min | 10-20 min | 20-30 min | 30-40 min | 40-50 min | 50-60 min |
| 5 | 0 | 2 | 2 | 5 | 3.5 | 0 |
| Avg. | 2 | 3 | 3.6 | 1 | 1.8 | 0.1 |
| Std. Dev. | 4.22 | 5.33 | 6.59 | 2.11 | 2.18 | 0.21 |

Figure 5:
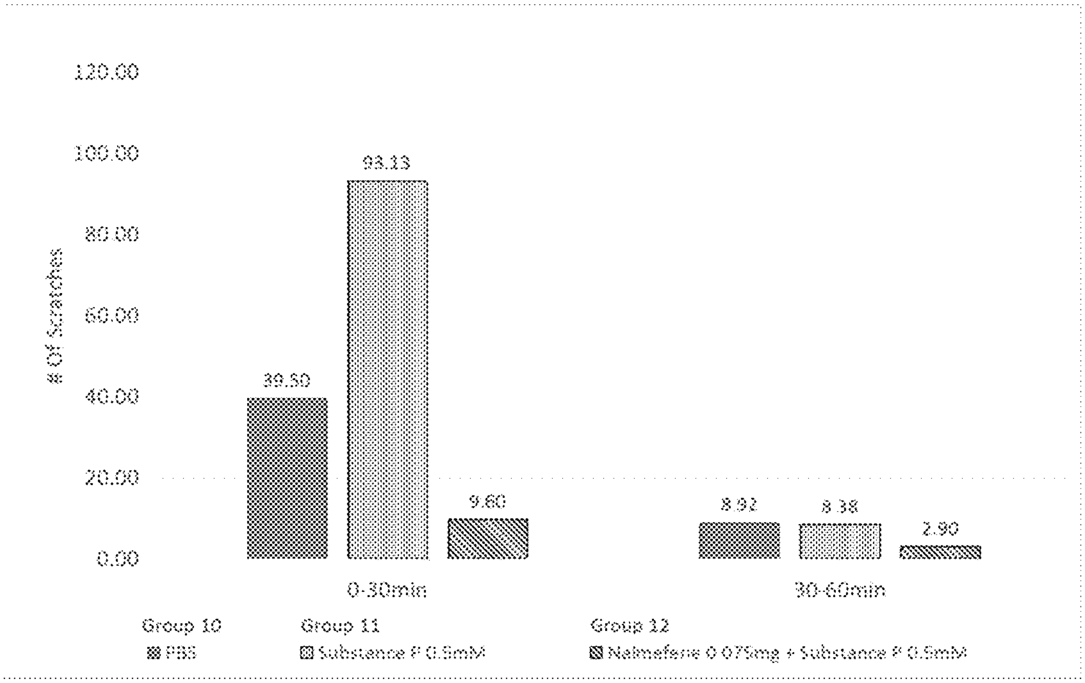
FIG. 5 is a bar graph illustrating the average number of scratches for Group 10, 11, and 12 mice at 0-30 minutes and 30-60 minutes.

The number of scratches per 0-30 minute and 30-60 minute time intervals is given below in Table 4 for Group 10 (PBS), Group 11 (0.5 mM SP), and Group 12 (0.75 mg nalmefene). The data is also shown graphically in FIG. 5.

The data demonstrates that the ability of nalmefene to control scratching behavior, and by extension pruritus, is maintained over the hour.

TABLE 4

| Scratches per 0-30, 30-60 Minutes | | | |
|---|---|---|---|
| | No. | 0-30 min | 30-60 min |
| Group 10, PBS | 1 | 6 | 1.5 |
| | 2 | 74 | 22.5 |
| | 3 | 77.5 | 13 |
| | 4 | 41 | 13 |
| | 5 | 3 | 0 |
| | 6 | 11.5 | 3.5 |
| | Avg. | 35.5 | 8.92 |
| | Std. Dev. | 32.41 | 8.33 |
| Group 11, SP 0.5 mM | 1 | 119 | 19.5 |
| | 2 | 67 | 5.5 |
| | 3 | 94.5 | 2.5 |
| | 4 | 69.5 | 6 |
| | Avg. | 87.5 | 8.38 |
| | Std. Dev. | 22.59 | 7.01 |
| Group 12, Nalmefene 0.75 mg | 1 | 10 | 1 |
| | 2 | 29 | 5 |
| | 3 | 0 | 0 |
| | 4 | 0 | 0 |
| | 5 | 4 | 8.5 |
| | Avg. | 8.6 | 2.9 |
| | Std. Dev. | 11.42 | 3.53 |

Example 4

Dose Escalation of SP

The SP dose administered to male C57BL/6 mice was escalated and itching was recorded for analysis. Group 13 (N=8) received ID injection of 135 μg SP on the right side of the rostral back. Group 14 (N=8) received ID injection of 233 μg SP on the right side of the rostral back. At T0-60, immediately following dose administration, a camera began recording to monitor itching behavior. At T60, the final itching assessment was completed, camera recording ended, and the study was concluded.

The recordings were reviewed to calculate itching behavior. Two research associates reviewed the recordings and counted the number of scratches for each mouse during the 60-minute collection time. The mean of the two observations were recorded as the number of scratches per 60 minutes.

The study design is set forth below in Table 5, and the mean scratch counts are given in Table 6.

TABLE 5

Study Design, Example 3

| Dose Group | N= | Test | Dose (μg) | Dose Conc. (mg/mL) | Dose Vol. (mL) | Itching Assess. Obs. |
|---|---|---|---|---|---|---|
| 14 (Mid Dose) | 8 | SP in saline | 135 | 2.701 | 0.05 | T0-T60 |
| 15 (High Dose) | 8 | SP in saline | 233 | 4.66 | 0.05 | |

Figure 6:
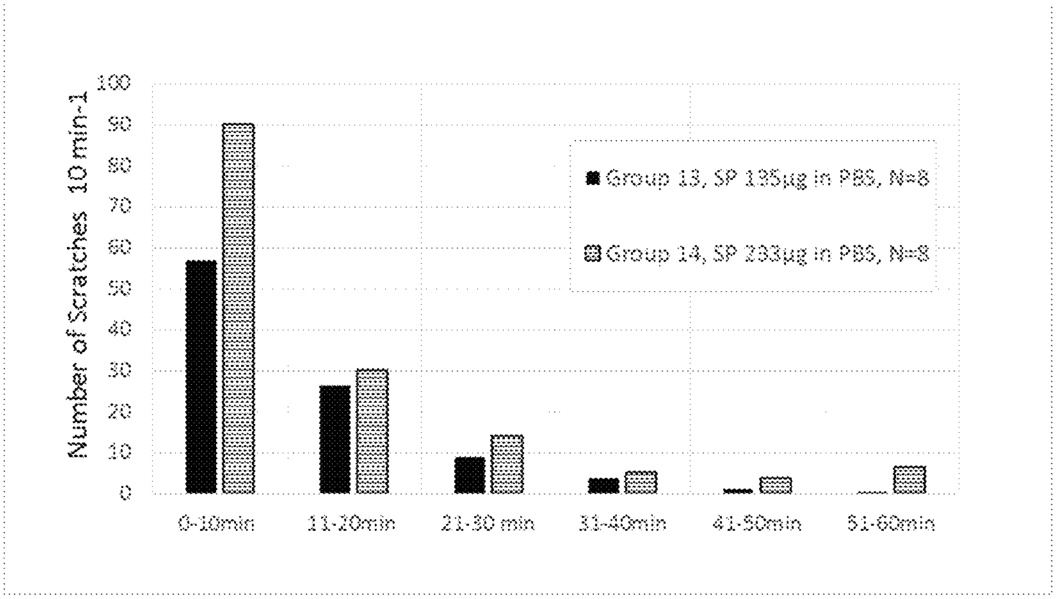
FIG. 6 is a bar graph illustrating the number of scratches per 10 minute intervals after administration of low dose SP (Group 13) and high dose SP (Group 14).

The scratching over time was observed per 10 minute time period for each animal tested. The data is set forth below in Table 6 and is shown graphically in FIG. 6.

TABLE 6

Mean Scratch Count

| Group | No. | 0-10 min | 10-20 min | 20-30 min | 30-40 min | 40-50 min | 50-60 min |
|---|---|---|---|---|---|---|---|
| 13 | 1 | 57 | 36 | 2 | 0.5 | 3.5 | 2 |
| | 2 | 21.5 | 23 | 12.5 | 12 | 0 | 0.5 |
| | 3 | 91 | 41 | 22.5 | 0 | 0 | 0 |
| | 4 | 72 | 9.5 | 23 | 2 | 0 | 0 |
| | 5 | 127 | 53.5 | 0 | 0 | 0 | 0 |
| | 6 | 58 | 41.5 | 4 | 15 | 0 | 0 |
| | 7 | 5.5 | 0 | 7 | 0 | 5 | 0 |
| | 8 | 22 | 7 | 0 | 0 | 0 | 0 |
| | Avg. | 56.75 | 26.44 | 8.88 | 3.69 | 1.06 | 0.31 |
| | Std. Dev. | 39.02 | 18.76 | 9.17 | 5.94 | 1.94 | 0.68 |
| 14 | 1 | 123 | 56.5 | 7 | 0 | 3 | 8 |
| | 2 | 131.5 | 32 | 6 | 3 | 0 | 0 |
| | 3 | 108 | 42 | 27 | 5 | 4 | 2 |
| | 4 | 85.5 | 33 | 21.5 | 16.5 | 7.5 | 33 |
| | 5 | 8 | 6 | 5 | 8 | 0 | 1 |
| | 6 | 33 | 9 | 10.5 | 4 | 0 | 0 |
| | 7 | 145 | 35 | 16 | 0 | 1 | 5.5 |
| | 8 | 85 | 27 | 18.5 | 5 | 13 | 1 |
| | Avg. | 89.88 | 30.06 | 13.94 | 5.19 | 3.56 | 6.31 |
| | Std. Dev. | 46.44 | 15.96 | 7.8 | 5.11 | 4.47 | 10.77 |

Example 5

Measuring Plasma Concentration in Dogs

Figure 7:
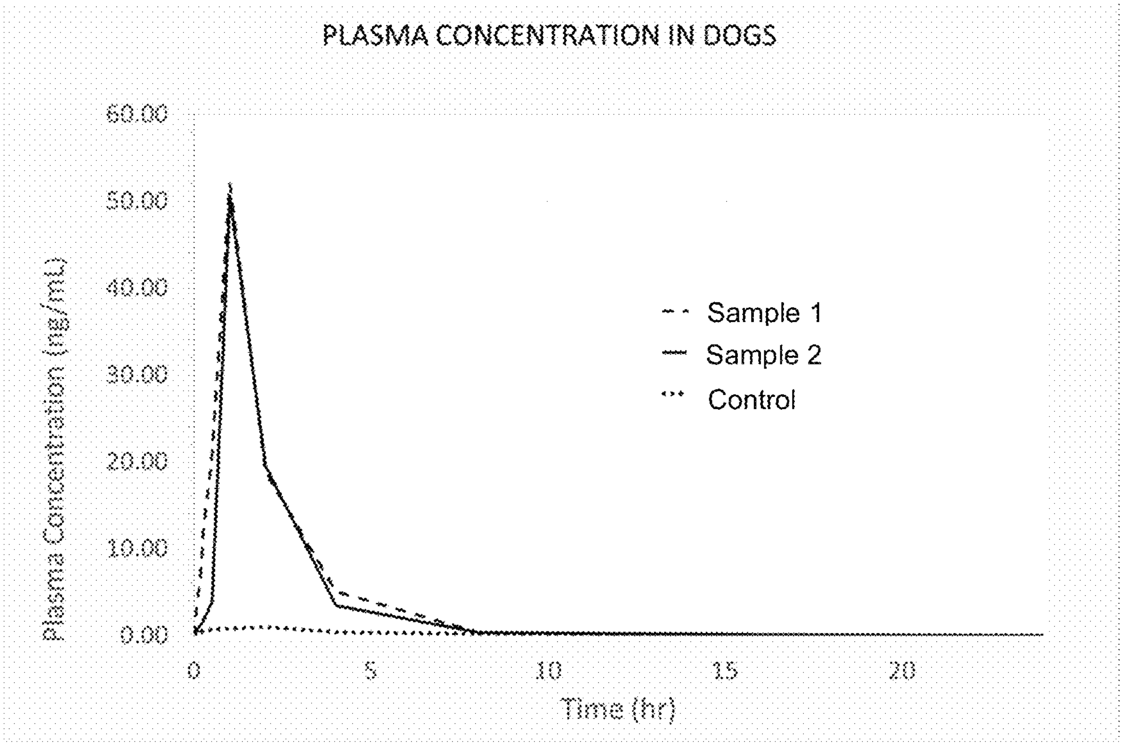
FIG. 7 is a line graph illustrating plasma concentration over a time period of 20 hours.
Figure 8:
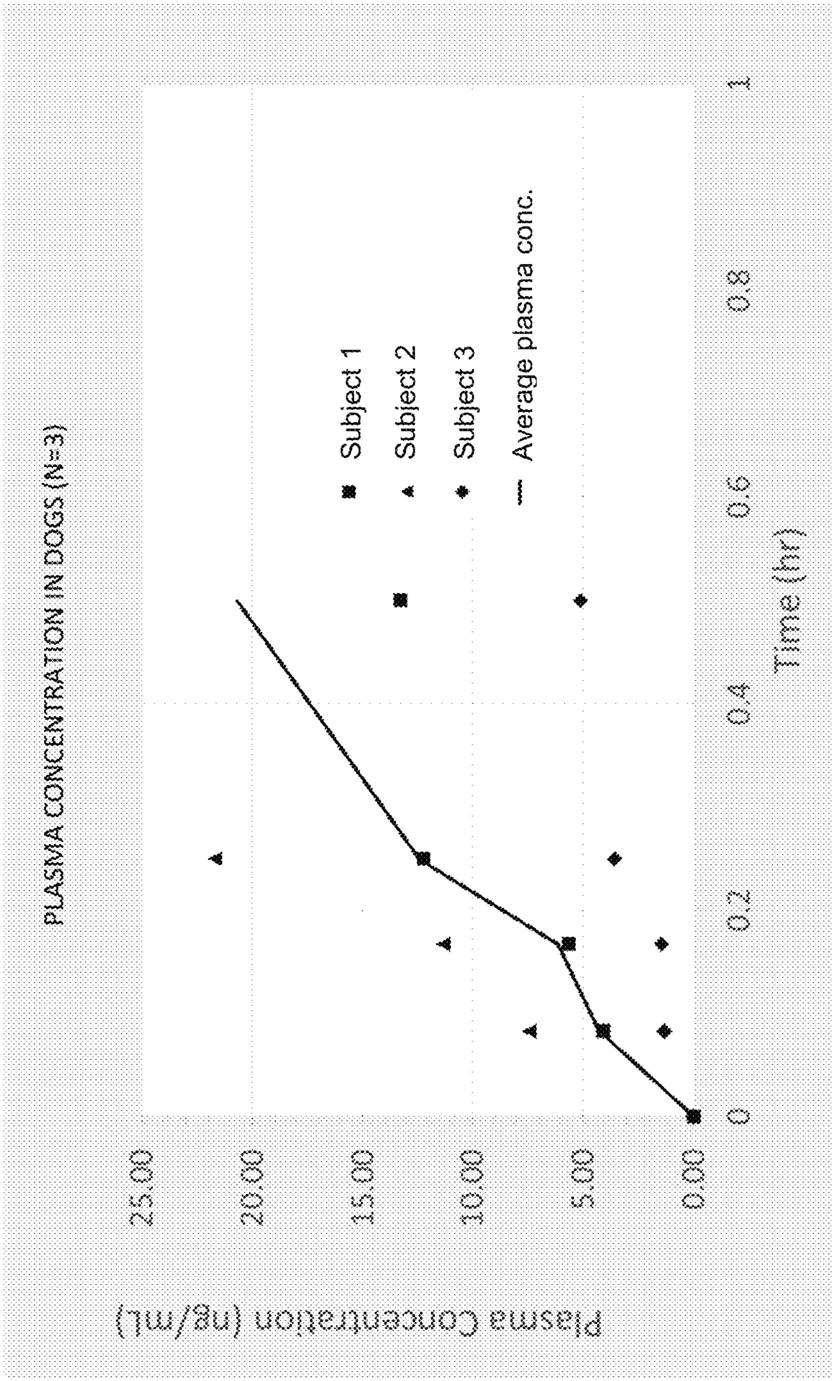
FIG. 8 is a line graph illustrating plasma concentration over a time period of 1 hour.

Testing was performed using dogs to evaluate plasma concentration of nalmefene over time when delivered using exemplary film devices. Two exemplary film devices were tested. A control tablet was also tested for comparison. An 18 mg tablet was administered to the dogs followed by a 10 mL flush with drinking water. The nalmefene film devices were administered buccally. Two 8 mg films were administered simultaneously for a total dosage of 16 mg. The dogs were anesthetized and the film devices put in place thereafter. Blood sampling was performed as follows: pre-dose, 5 mins, 10 mins, 15 mins, 30 mins, 1 hour, 2 hours, 4 hours, 8 hours, 12 hours, 24 hours and 48 hours post dose. FIG. 7 is a line graph showing the plasma concentration in ng/mL for two film device samples and for the control tablet for a time period of 20 hours. As can be seen in the FIG. 7, the plasma concentration of nalmefene that was administered using film devices was up to 50 ng/mL within an hour. The plasma concentration of nalmefene that was administered using tablets never reached over 1 ng/mL. Thus, higher concentrations of nalmefene were achievable much more rapidly using the film devices. FIG. 8 is a line graph showing the plasma concentration in ng/mL for 3 dogs, each of which was administered nalmefene using an exemplary film device. FIG. 8 shows plasma concentration for a time period of 1 hour, which is helpful in understanding how rapidly nalmefene can be delivered using exemplary film devices. The individual plasma concentration data points for each dog are shown. The plotted line is the average plasma concentration of the three dogs. As can be seen in FIG. 8, the average plasma concentration of nalmefene approached 5 ng/mL within 5 minutes. Within 10 minutes, the average plasma concentration of nalmefene was over 5 ng/mL.

REFERENCES

1. ESRD Patients, in 2013—A Global Perspective. *Fresenius Medical Care,* 2014.
2. Pisani, R L, et al, "Pruritus in Hemodialysis patients: Intl Results from Dialysis Outcomes and Practical Pattern Study," *Nephrol. Dial. Transplant,* 2006, 21:3495-3505.
3. Coresh, et al., *JAMA* (2007), 298:2038-47.
4. Revex® Prescribing Information, https://www.accessdata.fda.ciov/drucisatfda_docs/label/2006/020459 s006lbl.pdf
5. Cara Therapeutics Doses First Patient in Second Pivotal Phase 3 Efficacy Trial of KORSUVA™ (CR845/difelikefalin) Injection in Hemodialysis Patients with Chronic Kidney Disease-Associated Pruritus, Aug. 7, 2018, Press Release. http://ir.caratherapeutics.com/news-releases/news-release-details/cara-therapeutics-doses-first-patient-second-pivotal-phase-3
6. Trevi Therapeutics Raises $50 Million Series C Financing Led by New Enterprise Associates, Jul. 17, 2017 Press Release. http://www.trevitherapeutics.com/news/view/42
7. Ko M C, Lee H, Song M S, Sobczyk-Kojiro K, Mosberg H I, Kishioka S, "Activation of kappa-opioid receptors inhibits pruritus evoked by subcutaneous or intrathecal administration of morphine in monkeys," *J Pharmacol. Exp. Ther.* 2003; 305:173-9.
8. Lee H, Naughton N N, Woods J H, Ko M C. Effects of butorphanol on morphine-induced itch and analgesia in primates. *Anesthesiology.* 2007; 107:478-85.
9. Charuluxananan S, Kyokong O, Somboonviboon W, Lertmaharit S, Ngamprasertwong P, Nimcharoendee K. "Nalbuphine versus Propofol for treatment of—intrathecal morphine-induced pruritus after cesarean delivery," *Anesth Analg.* 2001; 93:162-5.
10. Charuluxananan S, Kyokong O, Somboonviboon W, Narasethakamol A, Promlok P., "Nalbuphine versus ondansetron for prevention of intrathecal morphine-induced pruritus after cesarean delivery," *Anesth Analg.* 2003; 96:1789-93.

What is claimed is:

1. A method of treating pruritus in a subject, the method comprising transmucosally administering to a subject in need of such treatment a therapeutically effective amount of nalmefene or a pharmaceutically acceptable salt thereof, wherein the nalmefene or pharmaceutically acceptable nalmefene salt is administered through a single layer, self-supporting, mucoadhesive film, the film comprising:

a first discrete domain and a second discrete domain;

wherein the first discrete domain comprises 5 to 100 weight percent polymer matrix comprising hydroxy propyl methyl cellulose (HPMC) and sodium carboxymethyl cellulose (NaCMC) based on the total weight of the first discrete domain, and further comprises one or more of a permeation enhancer, and pH adjusting buffer, wherein the second discrete domain comprises nalmefene or a pharmaceutically acceptable nalmefene salt;

wherein the second discrete domain is non-self-supporting; and wherein the local pH of the first discrete domain is in a range of 3.5 to 8.5, and the local pH of the second discrete domain is in a range of 4 to 9.

2. The method of claim 1, wherein the subject has pruritus as a symptom of chronic kidney disease, reduced renal function, liver disease, prurigo nodularis, or combinations thereof.

3. The method of claim 1, wherein treatment of pruritus decreases the level of Substance P in the subject.

4. The method of claim 1, wherein the therapeutically effective amount comprises about 1 to about 32 mg nalmefene or pharmaceutically acceptable nalmefene salt.

5. The method of claim 1, wherein about 1 to about 8 mg of the nalmefene or pharmaceutically acceptable nalmefene salt is administered to the subject once a day and is then titrated to an effective dose.

6. The method of claim 1, wherein about 1 to about 8 mg of the nalmefene or pharmaceutically acceptable nalmefene salt is administered to the subject as an initial dose twice a day, and is then titrated to an effective dose of about 5 to about 32 mg.

7. The method of claim 1, wherein the transmucosal administration is selected from buccal administration or sublingual administration, which delivers about 1 to about 32 mg nalmefene or pharmaceutically acceptable nalmefene salt to the bloodstream of the subject in less than about 5, 30 or 60 minutes.

8. The method of claim 1, wherein the sublingual or buccal administration delivers about 1 to about 5 ng/mL nalmefene or pharmaceutically acceptable nalmefene salt to the bloodstream of the subject within about 5 minutes.

9. The method of claim 1, wherein a blood $C_{max}$ of the nalmefene or pharmaceutically acceptable nalmefene salt after administration is about 1 to about 50 ng/ml.

10. The method of claim 1, wherein a blood AUC at time 0-infinity after administration of the nalmefene or pharmaceutically acceptable nalmefene salt is about 5 to about 500 ng-hr/mL.

11. The method of claim 1, wherein the nalmefene or pharmaceutically acceptable nalmefene salt is at least about 50% dialyzable.

12. The method of claim 1, wherein the subject is a human, and the plasma concentration in the subject after administration is about 0.25 to about 10 ng/mL.

13. The method of claim 1, wherein the plasma concentration of nalmefene in the subject after administration is about 0.1 to about 25 ng/mL.

* * * * *